United States Patent
Qureshi

(10) Patent No.: US 12,193,866 B1
(45) Date of Patent: Jan. 14, 2025

(54) INTRAOSSEOUS AND INTRAMEDULLARY VISUALIZATION

(71) Applicant: Abid Qureshi, Los Altos, CA (US)

(72) Inventor: Abid Qureshi, Walnut Creek, CA (US)

( * ) Notice: Subject to any disclaimer, the term of this patent is extended or adjusted under 35 U.S.C. 154(b) by 72 days.

(21) Appl. No.: 15/985,402

(22) Filed: May 21, 2018

Related U.S. Application Data

(60) Provisional application No. 62/511,953, filed on May 26, 2017.

(51) Int. Cl.
| | |
|---|---|
| *A61B 6/00* | (2024.01) |
| *A61B 6/40* | (2024.01) |
| *A61B 6/42* | (2024.01) |
| *A61B 6/46* | (2024.01) |
| *A61B 34/20* | (2016.01) |
| *A61B 90/00* | (2016.01) |

(52) U.S. Cl.
CPC ............ *A61B 6/547* (2013.01); *A61B 6/4208* (2013.01); *A61B 6/4429* (2013.01); *A61B 6/461* (2013.01); *A61B 6/40* (2013.01); *A61B 34/20* (2016.02); *A61B 2090/3782* (2016.02)

(58) Field of Classification Search
CPC ....... A61B 6/547; A61B 6/461; A61B 6/4208; A61B 6/4429; A61B 34/20; A61B 6/40; A61B 5/6878; A61B 2018/00565; A61B 6/505; A61B 8/0875
See application file for complete search history.

(56) References Cited

U.S. PATENT DOCUMENTS

| | | | | |
|---|---|---|---|---|
| 5,423,850 | A * | 6/1995 | Berger | A61B 17/7225 604/96.01 |
| 9,770,278 | B2 * | 9/2017 | Lappin | A61B 17/8897 |
| 2003/0078495 | A1 * | 4/2003 | Goodwin | A61B 8/0875 600/424 |
| 2003/0225331 | A1 * | 12/2003 | Diederich | A61B 18/04 600/437 |
| 2004/0186368 | A1 * | 9/2004 | Ramzipoor | A61B 1/00082 600/407 |
| 2008/0091109 | A1 * | 4/2008 | Abraham | A61B 8/445 600/463 |
| 2008/0183080 | A1 * | 7/2008 | Abraham | A61B 1/3132 600/466 |
| 2011/0077525 | A1 * | 3/2011 | Baraso | A61B 8/12 600/459 |
| 2011/0208062 | A1 * | 8/2011 | Baraso | A61B 34/76 600/459 |
| 2012/0265186 | A1 * | 10/2012 | Burger | A61B 18/02 606/21 |
| 2012/0302875 | A1 * | 11/2012 | Kohring | A61B 1/05 600/424 |
| 2015/0073562 | A1 * | 3/2015 | Landon | A61F 2/3886 623/20.34 |
| 2015/0297246 | A1 * | 10/2015 | Patel | A61B 17/3478 606/79 |
| 2016/0310091 | A1 * | 10/2016 | Shimizu | A61B 6/12 |
| 2018/0140311 | A1 * | 5/2018 | Winshtein | A61B 17/1707 |
| 2018/0168539 | A1 * | 6/2018 | Singh | A61B 1/317 |
| 2019/0110833 | A1 * | 4/2019 | Pellegrino | A61B 18/1206 |
| 2019/0142528 | A1 * | 5/2019 | Vertikov | A61B 8/488 600/424 |
| 2020/0281659 | A1 * | 9/2020 | Kheradpir | A61B 34/20 |

* cited by examiner

*Primary Examiner* — Serkan Akar
*Assistant Examiner* — Aminah Asghar
(74) *Attorney, Agent, or Firm* — Los Altos Law

(57) ABSTRACT

An intramedullary cavity assembly includes a guide wire, a cannula having a trocar tip, emitters, sensors, exuding ports, and withdrawing ports. The emitter sends radiation into intramedullary tissue. The sensors, which detect effects thereof, include cameras or other radiation detectors. The assembly directs movement of the guide wire, and can exude/withdraw bodily fluids. Robotic control inputs/outputs, including a visualization element, operate the assembly. The guide wire is steerable from outside the body, and is capped with a trocar cannula, having surfaces transparent to energies used for visualization and operation. The visualization element includes computing devices, which receive sensor information, process it, and present it, so medical personnel can readily understand a 3D assessment of the assembly and intramedullary cavity. Medical personnel operate the assembly to emit energy or substances into tissues nearby, thus readily moving the assembly within the body and delivering treatment inside the body.

8 Claims, 4 Drawing Sheets

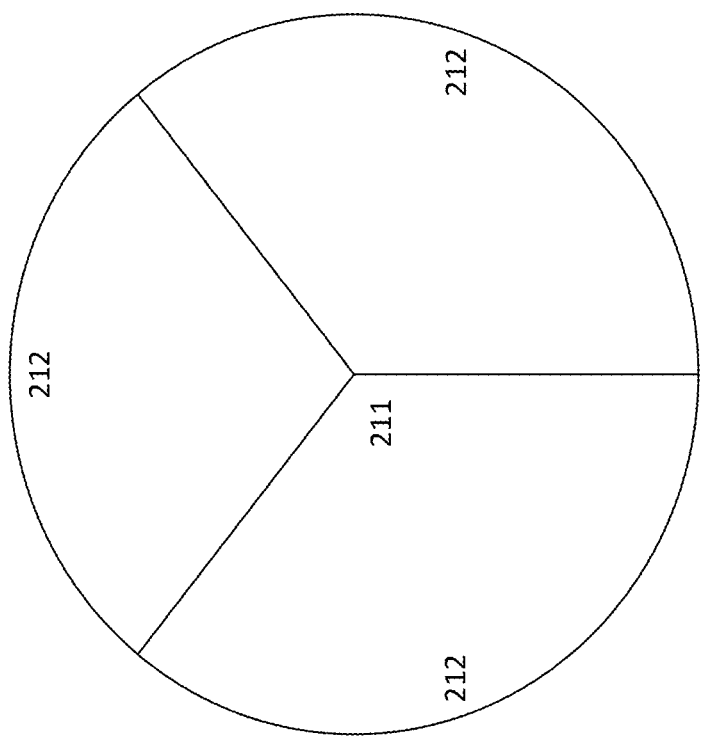

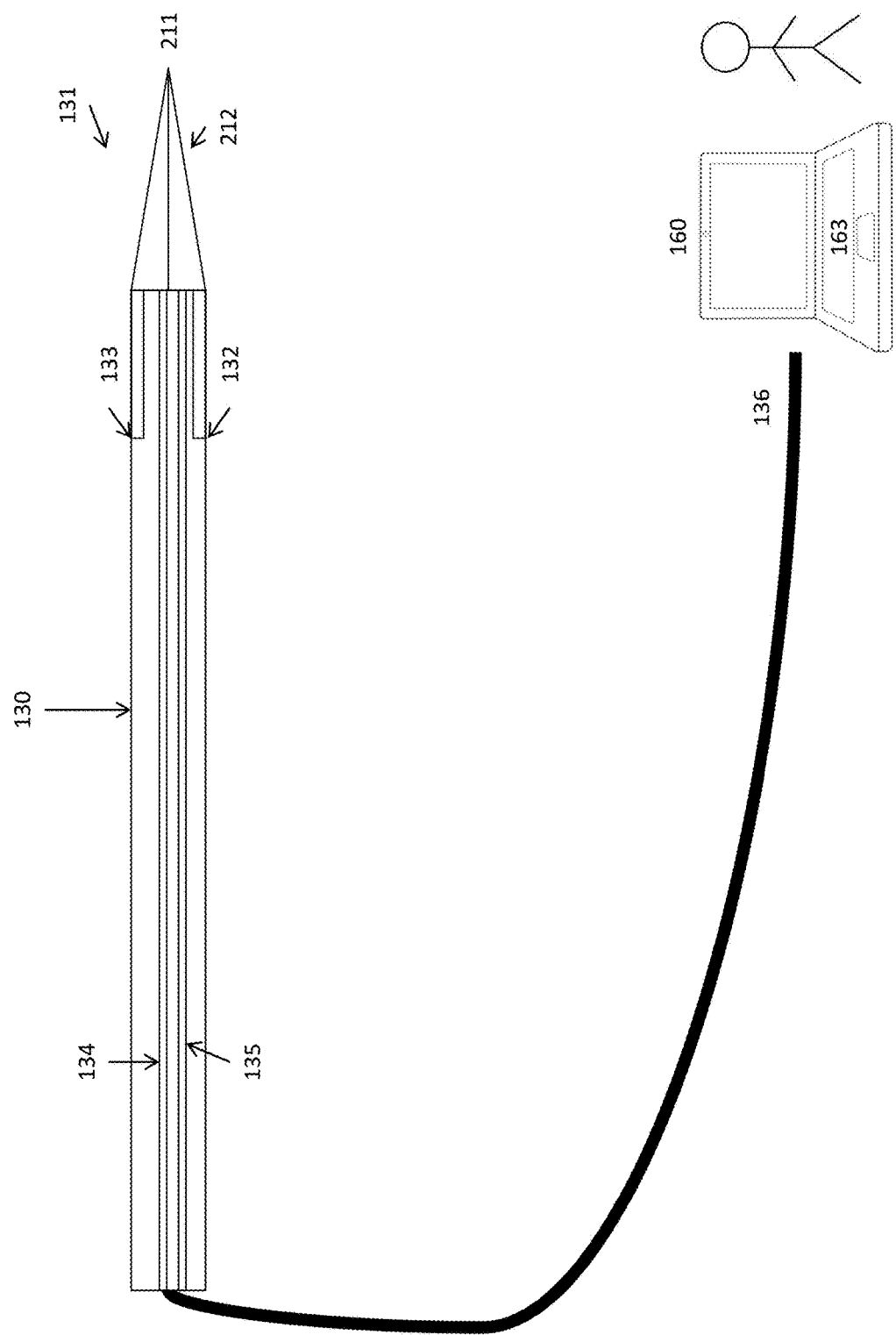

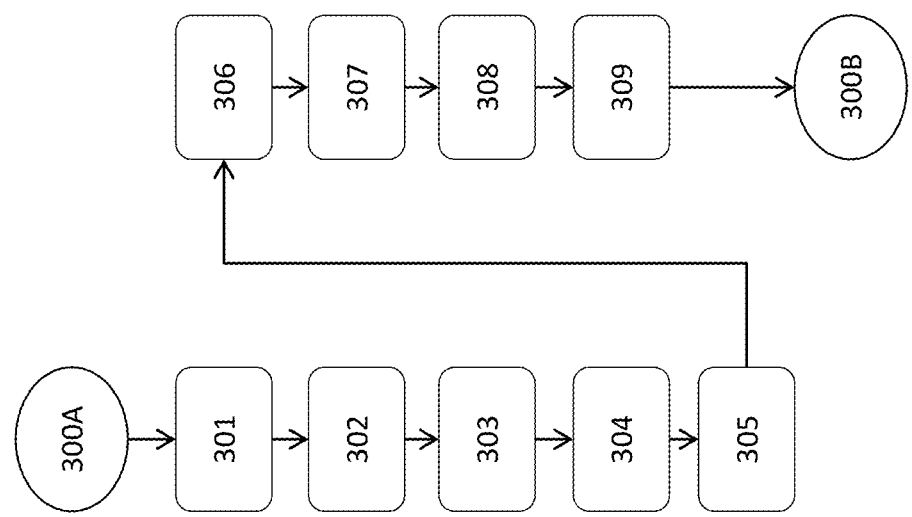

INTRAOSSEOUS AND INTRAMEDULLARY VISUALIZATION

This Application describes technologies that can be used with inventions, and other technologies, described in one or more of the following documents. These documents are sometimes referred to herein as the "Included Disclosures," the "Incorporated Documents," or variants thereof. Each and every one of these documents, as well as all documents cited therein, are hereby incorporated by reference as if fully recited herein. This application claims priority of each and every one of these documents, to the fullest extent possible, and also incorporates all other documents which any of those documents references.
1. U.S. Provisional Appl. 62/511,953, filed May 26, 2017 naming inventor Abid QURESHI, titled "Intraosseous and intramedullary visualization"
2. "Novel Concept, Method, Application and tools for Intraosseous visualization and fixation of fractures and bone lesions", a 3-page document dated Apr. 2, 2017, authored by Abid QURESHI, M.D., not published, a technical appendix to the US Provisional Application named above.

BACKGROUND

FIELD OF THE DISCLOSURE This Application generally describes techniques relating to intraosseous and intramedullary visualization and operation, and other technologies. For example, this Application describes techniques relating to visualization of, and operation on, internal bone structure, notwithstanding obstacles thereto presented by the nature of that bone structure. This Application also describes other and further techniques.

RELATED ART Medical personnel are sometimes called upon to correct, or at least ameliorate the effect of, bone fractures and bony lesions, included but not limited to osteoporosis and avascular necrosis of bone. One problem is that external corrections, such as affixing extraosseous structures (such as plates, screws, wires, coupling to other bony or non-bony structures, or combinations thereof), or other extraosseous techniques, might impose damage or modification to the bone, and might leave residual structures that affect bone regrowth. Another problem is that internal corrections, such as insertion of intramedullary supports (such as intramedullary nails, rods, wires, or combinations thereof) or other intraosseous techniques, might when conducted involve only limited information available to medical personnel, which might have the effect of less than optimal repair. For example, internal correction might involve control of an intramedullary support or another internal medical device; it would be useful for medical personnel to be able to clearly identify where the device is placed. For another example, internal correction might involve coupling an internal medical device to an external support; it would be useful for medical personnel to be able to clearly identify where the device is connected.

Known methods for presenting information from inside the body, to medical personnel operating without extensive invasion thereof, are subject to the drawback that they are limited in capability by the nature of intramedullary cavities. Intramedullary cavities might contain blood, bone fragments and bony structures, fats and other lipids, or other biological or chemical items that might interfere with visualization or operation. Because intramedullary cavities might contain bone fragments and bony structures (such as cancellous bone), movement within those cavities might be subject to the danger of damaging the body (or the bone structure itself), might be subject to limited freedom of action (as if in a maze rather than a highway), or might be subject to significant doubt by medical personnel with respect to the location of medical devices while using them.

Accordingly, each of these issues, as well as other possible considerations, might cause difficulty in aspects of services performed by medical personnel, particularly when correcting bone fractures and bony lesions, included but not limited to osteoporosis and avascular necrosis of bone.

SUMMARY OF THE DISCLOSURE

In one embodiment, an assembly usable with intramedullary procedures, such as including a guide wire, can include an emitter and one or more sensors. The emitter can be capable of sending (nonionizing or ionizing) radiation or other energy into surrounding intramedullary tissue or structures, bony tissue or structures, or extraosseous tissue or structures. The sensors (such as cameras or other sensors) can be capable of detecting effects of that radiation. Moreover, sensors outside the body can be capable of detecting effects of that nonionizing or ionizing radiation (such as due to the emissions of fluoroscopic or radioactive substances). The assembly can include elements for directing the guide wire when inserted into or through an extraosseous region, into or through a bone or bony structure, or into or through an intramedullary structure or tissue. The assembly can include elements for exuding or withdrawing bodily fluids or tissues, such as blood, bone marrow, or otherwise.

In one embodiment, the assembly can be operated in conjunction with robotic control inputs and outputs. The control outputs can include a visualization element, capable of receiving information input from the sensors, processing that information and presenting the processed information to medical personnel, and controlling information and energy output by the emitter in response to that processing and those medical personnel. The control inputs can include instructions from medical personnel to direct the assembly's movement, operation of the emitter, type of information processing and presentation, and operation of the sensor.

The control inputs can include a guide wire, capable of positioning and moving the assembly within the body. For example, the guide wire can be semi-rigid, or rigid and flexible, and steerable within the body from a point external to the body. The guide wire can be coupled to a cannula and a trocar tip, which can be suitable for insertion into, and penetration of, an extraosseous region, into or through a bone or bony structure, or into or through an intramedullary structure or tissue. The trocar tip can include surfaces that can be substantially transparent to energies and frequencies used for visualization. The cannula can also include elements for operation by medical personnel to perform operations within the body from outside of it.

In one embodiment, the visualization element can include one or more computing devices (such as processors and memory), including program information and data interpretable by the processors to receive information from the sensors, process that information, and present the processed information to medical personnel. For example, the computing devices can receive information from one or more sensors, deduce the position and orientation of the assembly and of elements and structures in or near the intramedullary cavity, and can present a unified picture of the assembly and the intramedullary cavity. This can have the effect that medical personnel can conveniently and readily understand a three-dimensional (3D) assessment of the assembly and the intramedullary cavity.

For example, the sensors can include multiple cameras coupled to the assembly. These multiple cameras optionally can be coupled to the assembly at differing angles or locations; with differing acuity, focal length, or precision; with differing sensing frequencies (such as infrared, optical, ultraviolet, or otherwise); or with other differing configuration features or parameters. The multiple cameras can be controlled by medical personnel to operate cooperatively, such as by adjusting their configuration features or parameters.

For another example, the visualization element can include optical tomography, such as using optical tomographic elements, with the effect of providing a 3D image of the assembly and the intramedullary cavity. The optical tomographic elements can include tomographic sensors disposed inside and/or outside the body, with the effect of providing signals on which tomographic processing can operate. The tomographic sensors can be coupled to one or more computing elements disposed to conduct optical tomography. For example, the visualization element can be disposed to receive illumination at infrared frequencies from the intramedullary cavity, and can be disposed to present that infrared information in visual frequencies, such as a false-color image, to medical personnel. In such cases, the assembly can include an infrared light-emitting diode (LED), from which the trocar tip emits electromagnetic energy at infrared or other frequencies. In such cases, the assembly can include an infrared sensor, optionally coupled to a photomultiplier or other image-enhancing device, from which the sensor couples information gleaned from infrared reflection to a computing device, which provides a visualization on an output device, for viewing by medical personnel. In such cases, the visualization element can include program information and data suitable to present infalling infrared as a visual image in which greater measured intensity is shown as a brighter element or a higher visual frequency.

In one embodiment, the computing devices, or another set, can receive control signals and instructions from medical personnel to operate the assembly. For example, operating the assembly can include moving the assembly, penetrating extraosseous tissue or structures, penetrating bone or bony structures, and penetrating one or more portions of the intramedullary cavity. For another example, operating the assembly can include emitting energy (electromagnetic or otherwise), or substances (active or inactive; biological, chemical, radiological, or otherwise) into tissues near the assembly. This can have the effect that medical personnel can conveniently and perform movement of the assembly with readily ease. This can also have the effect that medical personnel can conveniently and readily deliver treatment to inside the body, without extensive invasion thereof.

In one embodiment, medical personnel can visualize the microenvironment within or near the intramedullary cavity; use that visualization to obtain information about or understand the homeostasis of the bone marrow at a microscopic level; and use that information or understanding to identify different therapies based on patterns.

In one embodiment, medical personnel can take advantage of the possibility that stem cells are produced in bone marrow; that is, the possibility that at least a portion of the process of producing stem cells is based on actions in bone marrow. In such cases, when stem cells produced in bone marrow go awry, they can migrate to other parts of the body, such as different organs, and cause cancers.

In one embodiment, medical personnel can dispose timed-release substances in the bone marrow. This can have the effect of avoiding chemotherapy, such as when the timed-release substances provide repair of stem cells or culling of damaged stem cells, preventing damaged stem cells from migrating to other parts of the body and cancer consequently appearing in those other parts of the body. This can alternatively have the effect of avoiding damage from osteoporosis, such as when the timed-release substances provide repair of bone structure (or assistance to the bone structure in repairing itself).

BRIEF DESCRIPTION OF THE FIGURES

In the figures, like references generally indicate similar elements, although this is not strictly required.

FIG. 2 (collectively including FIGS. 2A and 2B) shows a conceptual drawing of an assembly. FIG. 2A shows a conceptual drawing of a front view. FIG. 2B shows a conceptual drawing of a cutaway view.

FIG. 3 shows a conceptual drawing of a method.

Figure 1:
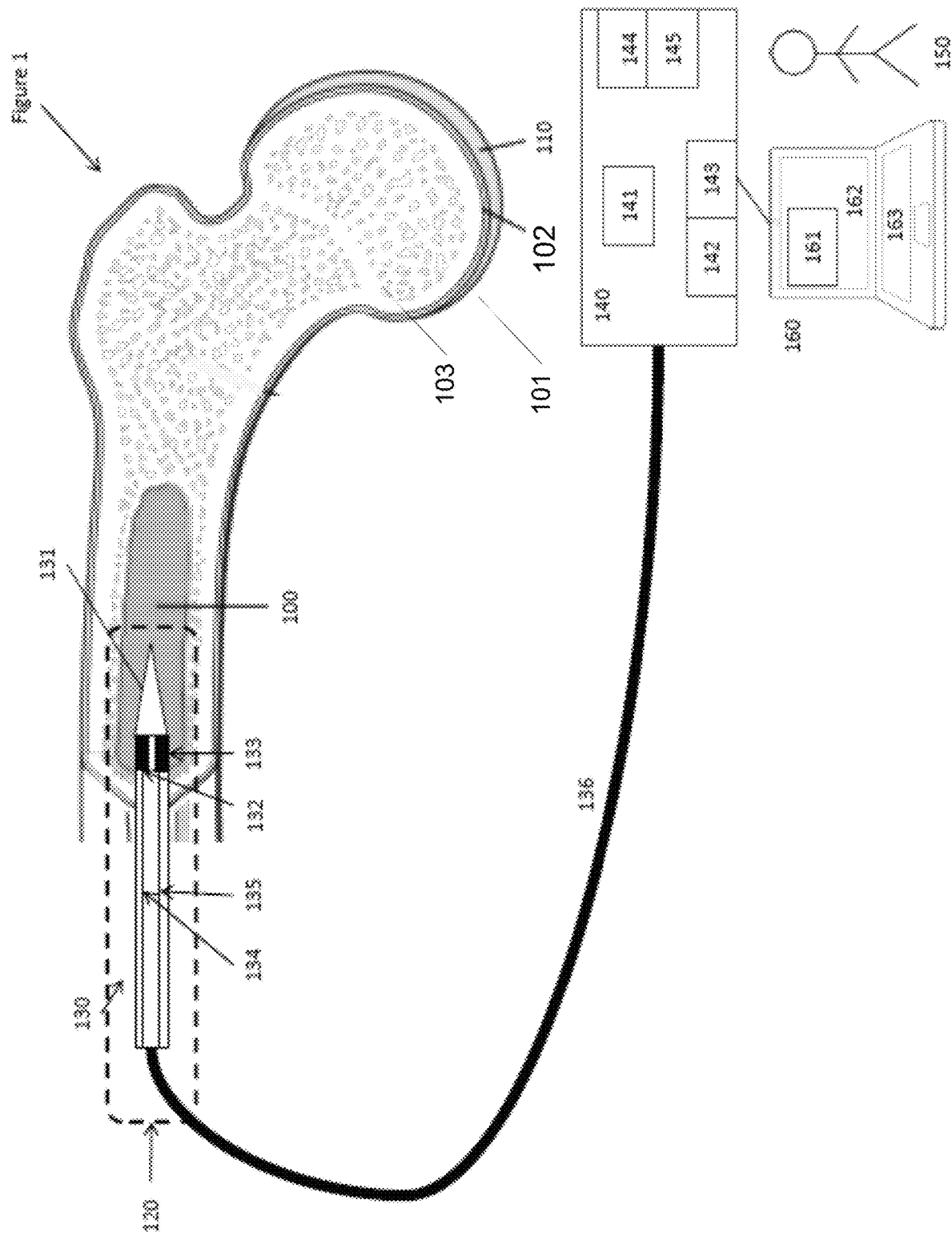
FIG. 1 shows a conceptual drawing of an assembly positioned in an intramedullary cavity.

After reading this Application, those skilled in the art would recognize that the figures are not necessarily (1) drawn to scale for construction, or (2) specify any particular location or order of construction.

DETAILED DESCRIPTION OF THE DISCLOSURE

Terms and Phrases

The phrase "bone or bony structure", and variants thereof, can include other substances or tissues closely related to bone and bony structures, such as bone subject to avascular necrosis or other necrosis, bone fragments, bone lesions, bone marrow or blood, cancellous bone, cartilage, fats and other lipids, necrotic or osteoporotic bone structures, or otherwise.

The phrase "visualization element", and variants thereof, can include the emitters (or external light sources), the sensors, and any associated devices. For example, the sensors can include one or more cameras, whether operating in visual or non-visual frequencies. For another example, the associated devices can include a control system, having one or more data transfer links, and one or more control links. For another example, the associated devices can include a computing device and memory, one or more input devices, and one or more output devices, the latter of which can present information to medical personnel.

Figures and Text

FIG. 1

FIG. 1 shows a conceptual drawing of a system.

The system can be described herein with respect to elements shown in the figures, such as:
an intramedullary cavity 100;
a bone structure 110;
an assembly 120;
a cannula 130, including at least a trocar tip 131, one or more emitters 132, one or more sensors 133, one or more exuding ports 134, one or more withdrawing ports 135, and a guide wire 136;
a control system 140, including at least a steering device 141, one or more data transfer links 142, one or more control links 143, one or more substance input conduits 144, one or more substance output conduits 145;

medical personnel 150; and one or more computing devices 160, including at least program and data memory 161, one or more output elements 162, and one or more input elements 163.

An intramedullary cavity 100 can be defined by a bone structure 110, such as a bone located in the arms or legs, a hip bone, or otherwise. Many bones 110 are substantially hollow—that is, they are not solid bone—but the intramedullary cavity 100 they define is not necessarily empty. For example, the intramedullary cavity 100 can include bone growths or bony structures within them. The intramedullary cavity 100 can also include blood, bone marrow, cancellous bone, fat, cancerous cells, stem cells, other cells, other biological matter, and other matter. The intramedullary cavity 100 can also include non-biological matter, such as possibly cement that had been earlier deposited as part of a procedure to replace a hip socket.

Although this Application primarily shows the intramedullary cavity 100 as a relatively long and thin cylindrical tube (such as in an arm bone or leg bone), and primarily shows the bone structure 110 as cleanly surrounding the intramedullary cavity 100, in the context of the invention, there is no particular reason for any such limitation. For example, a hip bone, or portion thereof, can include a relatively flat and dispersed intramedullary cavity 100, with a curved surrounding bone structure 110. Portions of the hip bone, or other bones, can have ill-defined intramedullary cavities 100, with surrounding bone structure 110 that is ill-defined in shape. Bone structures 110 can also exist within the intramedullary cavity 100, or can otherwise interfere with visualization of the intramedullary cavity 100.

An assembly 120 can be inserted into the intramedullary cavity 100, such as by drilling a hole at an end or a side of a bone structure 110, or by entry through a fracture if the bone structure 110 has been damaged. In cases in which the intramedullary cavity 100 includes substantial non-biological matter (such as cement, in cases in which the bone structure 110 has been repaired or replaced with a support), a hole can be drilled through the non-biological matter, or that non-biological matter can be abraded or dissolved.

The assembly 120 can include elements shown in the figure, such as: a cannula 130, trocar tip 131, having one or more emitters 132, one or more sensors 133, one or more exuding ports 134, one or more withdrawing ports 135, and a guide wire 136. As described herein, the emitters 132 and sensors 133 can include one or more cameras (operating in visual or non-visual frequencies), and can be coupled to one or more data transfer links 142 (in the control system 140) and one or more control links 143 (in the control system 140); the exuding ports 134 and withdrawing ports 135 can be coupled to one or more substance input conduits 144 (in the control system 140) and one or more substance output conduits 145 (in the control system 140); and the guide wire 136 can be coupled to a steering device 141 (in the control system 140).

Control System

The assembly 120 can also be coupled to a control system 140. The control system 140 can include one or more support elements, such as: the data transfer links 142 and control links 143, the substance input conduits 144 and substance output conduits 145, and the steering device 141.

The control system 140 can be used by medical personnel 150. The medical personnel 150 can use the control system 140 either with or without one or more computing devices 160.

The computing devices 160 can include elements shown in the figure, such as: program and data memory 161, one or more output elements 162, and one or more input elements 163.

Visualization

The emitters 132 can be capable of sending radiation or other energy into surrounding intramedullary tissue or structures, on bony tissue or structures, or extraosseous tissue or structures. In one embodiment, the emitters 132 can emit electromagnetic radiation into the cavity 100 near the assembly 120. The emitters 132 can either generate that electromagnetic radiation themselves (such as in response to electrical signals); or can transfer that electromagnetic radiation, such as using a fiber optic cable or other light piping device, from outside the body (or from outside the cavity 100) to inside the cavity 100. The sensors 133 can receive reflections, refractions, and any other returns from the cavity 100. The computing device 160 can determine the contents of the cavity 100 in response to any differences between the signal output by the emitters 132 and the signal input from the sensors 133.

For example, the emitters 132 can shine infrared light into the cavity 100, and the sensors 133 can measure reflections of that infrared light. The computing device 160 can provide processing of those reflections of that infrared light substantially like that of "night vision," or other photographic transforms performable on images from cameras, whether operating in visual or non-visual frequencies. For example, photographic transforms can be performed to obtain 3D imaging, such as responsive to stereoscopy or tomography. This can have the effect that the emitters 132 and sensors 133 can collectively provide information about contents of the intramedullary cavity 100, without losing information to the cavity's opacity to visible light.

The data transfer links 142 and control links 143 can be coupled to the emitters 132 and sensors 133. For example, the data transfer links 142 and control links 143 can be coupled to the computing device 160 or its memory 161. In such cases, the computing device 160 can receive information from the sensors 133 using the data transfer links 142, process them, and provide commands to the emitters 132 using the control links 143.

When the emitters 132 and sensors 133 are coupled to the data transfer links 142 and control links 143, the computing devices 160 can obtain information about the intramedullary cavity 100. For example, the computing devices 160 can use the control links 143 to direct the emitters 132 to illuminate the intramedullary cavity 100, such as in the infrared spectrum, the visual spectrum, or another set of electromagnetic frequencies. The computing devices 160 can use the control links 143 to direct the sensors 133 to send information using the data transfer links 142 back to the computing devices 160. Collectively, the emitters 132, sensors 133, and associated devices can be referred to as a visualization element for the system. Thus, the computing devices 160 can obtain information from reflections, or other effects on the emitted energy by the intramedullary cavity 100.

For a similar example, the computing devices 160 can glean information about the intramedullary cavity 100 using sonar or other sonic techniques, or otherwise.

The computing devices 160 can present information suitable to visualize the intramedullary cavity 100, using the output elements 163, to medical personnel 150. For example, when the emitters 132 illuminate the intramedullary cavity 100 and the sensors 133 measure reflections or refraction from tissues and bone structures 110 within the intramedullary cavity 100, the computing devices 160 can present an image that represents a view of (at least a portion of) the intramedullary cavity 100. This can have the effect that medical personnel 150 can obtain a three-dimensional (3D) view of the intramedullary cavity 100.

Treatment

The exuding ports 134 can be coupled to the substance input conduits 144, and the withdrawing ports 135 can be coupled to the substance output conduits 145. For example, the exuding ports 134 and the substance input conduits 144 can be disposed to receive medication from the substance input conduits 144, and to deposit that medication within the intramedullary cavity 100 to treat a condition therein, such as near the assembly 120.

For another example, the exuding ports 134 can be disposed to receive ablative, chemotherapeutic, pharmaceutical, reparative, or other substances from the substance input conduits 144, and to deposit those substances within or near the intramedullary cavity 100. This can have the effect of removing one or more untoward structures or tissues therein, also such as near the assembly 120. In such cases, the substances to be deposited can be combined with one or more delayed-release or timed-release agents, which can have the effect of providing a relatively shorter-term or relatively longerterm release into or near the intramedullary cavity 100.

For another example, the exuding ports 134 can be disposed to receive medication or other pharmaceutical substances, or other reparative substances, or other substances, to repair bone or bone structure within or near the intramedullary cavity 100, such as to repair or strengthen osteoporotic bone, or other relatively weaker bone. This can have the effect of strengthening bone or bone structure (or allowing the bone or bone structure to regrow and thereby strengthen itself). In such cases, the substances to be deposited can be combined with one or more delayed-release or timed-release agents, which can have the effect of providing a relatively shorter-term or relatively longerterm release into or near the intramedullary cavity 100.

The computing devices 160 can use the exuding ports 134 and the substance input conduits 144, or the withdrawing ports 135 and the substance output conduits 145, to affect the biological, chemical, or radiological environment of the intramedullary cavity 100, such as by exuding a substance whose presence is differentially absorbed or metabolized by different tissues in the intramedullary cavity 100 (such as a florescent or radiological substance). In such cases, the computing devices 160 can glean information about the intramedullary cavity 100 by noninvasively detecting or determining the differential uptake or metabolization of the exuded substance.

For example, the withdrawing ports 135 and the substance output conduits 145 can be disposed to receive tissue or other substances from within the intramedullary cavity 100 to conduct a biopsy, selective cell harvest, or other examination of any elements found therein. In such cases, the withdrawing ports 135 and the substance output conduits 145 can be disposed to harvest samples of bone marrow, stem cells, other tissue, and other cellular masses, as selected by medical personnel 150, from within the intramedullary cavity 100. In such cases, medical personnel 150 can select samples to harvest that are (A) known to be healthy, (B) unknown whether they are healthy or not, (C) known to be cancerous, diseased or otherwise unhealthy, (D) thought to be interfering with healthy bone growth or regrowth, or otherwise. In such cases, medical personnel 150 can select samples to harvest from selected locations, or which meet selected biological or chemical criteria (or radiological criteria, if pre-prepared with radiological markers).

For another example, the withdrawing ports 135 and the substance output conduits 145 can be disposed to receive the results of ablation or chemotherapeutic items, or to receive any cancerous, diseased, or otherwise untoward tissues or other elements, from within the intramedullary cavity 100, as part of an operation to remove those untoward tissues or other elements. In such cases, cells thought to be cancerous, diseased, or otherwise unhealthy can be ablated or treated with chemotherapeutic elements, and the results of ablation or chemotherapy can be removed using the withdrawing ports 135 and the substance output conduits 145. Some cancers can originate in bone marrow, such as leukemia and other blood cancers. When bone marrow cells or other tissue associated with those cancers are targeted, the results of tissue ablation or chemotherapy can be removed using the withdrawing ports 135 and the substance output conduits 145.

For another example, the withdrawing ports 135 and the substance output conduits 145 can be disposed to receive stem cells from bone marrow, or to receive other specialized cells from bone marrow or other intramedullary tissue. In such cases, the stem cells or other specialized cells can be identified with unique markers, using the exuding ports 134 and the substance input conduits 144 to exude a substance in the intramedullary cavity 100 (such as a florescent or radiological substance) whose presence is differentially absorbed or metabolized by those specialized cells. When identified with those unique markers, medical personnel 150 can visualize those specialized cells, and can use the withdrawing ports 135 and the substance output conduits 145 to specifically harvest (or to harvest with differentially greater effect) those specialized cells. This can have the effect of collecting those specialized cells in relatively larger or more purified samples.

The control links 143 can be coupled to the exuding ports 134 and withdrawing ports 135. Similar to the steering device 141 described herein, the exuding ports 134 and withdrawing ports 135 can be coupled to the computing device 160 or its memory 161. The computing device 160 can receive information from the input elements 162, which it can use to provide commands to, and receive responses from, the exuding ports 134 and withdrawing ports 135. This can have the effect that medical personnel 150 can operate the assembly's exuding ports 134 and withdrawing ports 135. In such cases, medical personnel 150 can deliver treatment to inside the body, without extensive invasion thereof.

Movement

The guide wire 136 can be coupled to the steering device 141. For example, the steering device 141 can be coupled to either the computing device 160 or its memory 161, or to the input elements 162. When the guide wire 136 is coupled to the steering device 141, medical personnel 150 can control the position and movement of the cannula 130.

In such cases, the input elements 162 either (A) can be coupled directly to the steering device 141, or (B) can be coupled indirectly to the steering device 141 using the computing device 160. In the first such case, medical personnel 150 can use the steering device 141 directly, to control the guide wire 136 and thus move the assembly 120. In the second such case, medical personnel 150 can direct the computing device 160 to control the guide wire 136 and thus move the assembly 120. In such cases, medical personnel 150 can visualize the intramedullary cavity 100 can observe the output elements 163 (such as an image display device), and can operate the steering device 141 using the input elements 162 to control the guide wire 136. Possibly, medical personnel 150 could instruct the computing device 160 to select the shortest route that avoids bone marrow.

As described herein, the guide wire 136 and the steering device 141 can be disposed to adjust the location or orientation of the cannula 130, such as moving the cannula 130 up or down, moving the cannula 130 right or left, moving the cannula 130 forward or backward, as well as other possible motions such as rotation or vibration of the cannula 130. Although this Application primarily describes the guide wire 136 and the steering device 141 with respect to location and orientation of the cannula 130, and although this Application primarily describes the cannula 130 with respect to control by the guide wire 136 and the steering device 141, in the context of the invention, there is no particular requirement for any such limitation.

Computing Devices

As described herein, the computing device 160 can be disposed to interpret instructions and data in its memory 161. The instructions and data can direct the computing device 160 to perform the functions described herein. When a selected device is coupled to the computing device 160, the computing device 160 can send requests to that selected device and receive responses from that selected device. When the selected device is configured to act on those requests and present its results as those responses, the computing device 160 can control the selected device, at least in part.

The computing device 160 can provide the output elements 136 with a visible image in response to the "night vision" image (described above with respect to visualization). In a first such case, the computing device 160 can provide a visible image in black/white, with relatively greater luminosity in those locations where infrared reflections are relatively greater. In a second such case, the computing device 160 can provide a visible image in false color, with relatively greater visible frequencies in those locations where infrared reflections are relatively greater. These images can subsequently be converted into colored images, and presented to medical personnel 150 as those colored images.

The computing device 160 can also include one or more application programs in its memory 161, and can be disposed to execute those application programs upon direction by medial personnel 150. For example, application programs can conduct a selected medical procedure, step by step, without substantial involvement by medical personnel 150. In such cases, the selected medical procedure can include a sequence of procedures that are conducted within the intramedullary cavity 100.

FIG. 2

FIG. 2 (collectively including FIGS. 2A and 2B) shows a conceptual drawing of an assembly. FIG. 2A shows a conceptual drawing of a front view. FIG. 2B shows a conceptual drawing of a cutaway view.

The assembly 120 can include elements shown in the figure, such as the elements shown with respect to FIG. 1, as well as:

first tissue 101 external to the bone, second tissue 102 integral to the bone, and third tissue 103 internal to the bone; and a trocar tip 131, a point 211, a set of surfaces 212.

The assembly 120 can include, capping or otherwise attached to the guide wire 136, the cannula 130 or other device that can be inserted into intramedullary cavity (or cavities) 100. The assembly 120 can be disposed so that the cannula 130 can be steered by the guide wire 136, such as up/down, right/left, and forward/backward (possibly involving movement of at least a portion of the guide wire 136 from side to side or forward/backward), as well as other possible motions such as rotation or vibration of the cannula 130. For example, the guide wire can be semi-rigid, or rigid and flexible, and steerable within the body from a point external to the body, as described herein.

For example, the cannula 130 can include a trocar tip 131, suitable for insertion into, and penetration of: first tissue 101 external to the bone (such as in an extraosseous region), second tissue 102 integral to the bone (such as the bone or its bony structure), and third tissue 103 internal to the bone (such as intramedullary tissue or other structures found in intramedullary cavities 100). In such cases, the trocar tip 131 can include a point 211 and a set of surfaces 212 disposed for penetration of tissue. The point 211 can be a relatively sharp element that can enter and penetrate bony corridors or other bony structure.

Emitters/Sensors

The cannula 130 can include the emitters 132 and the sensors 133, such as an infrared emitter or an emitter of another electromagnetic frequency (a microwave frequency, a visible frequency, or a near-ultraviolet frequency), and corresponding sensors 133 (such as one or more cameras, operating in one or more visual or non-visual frequencies). In such cases, the trocar tip 131 can have at least one of its surfaces 212 that can be substantially transparent to that frequency and those energies. This can have the effect that the trocar tip 131 can emit those energies into intramedullary cavities 100, those energies can interact with structures in the intramedullary cavities 100, and the sensors 133 can glean information with respect to that interaction. In alternative such cases, the trocar tip 131 can include one or more emitters 132 or sensors 133 located outside the surfaces 212, such as at a point 211 at the distal end of the trocar tip 131.

In alternative examples, the cannula 130 can include, disposed within, an emitter of other energies, such as sonic energy (sonar, ultrasound, or other wave mechanics operating on intramedullary tissue or other structures found in intramedullary cavities), or such as other energy suitable for visualization for operation by medical personnel, and corresponding sensors 133. In such alternative cases, the trocar tip 131 can include at least one surface that can be substantially transparent to those alternative energies, with the effect that the trocar tip 131 can emit those energies into the intramedullary cavity. In other alternative examples, the cannula 130 can include more than one such emitter, or an emitter of more than one such energy, and can be include more than one such transparent surface, or a surface transparent to more than one such energy.

In such cases, as described herein, the computing devices 160 can receive reflected illumination, or reflected sonic energy, or other indicators of tissue and bone structure 110 in the intramedullary cavity 100. The computing devices 160 can present information representative of the 3D structure of the intramedullary cavity 100, using the output elements 163, to medical personnel 150. In such cases, the output elements 163 can present that information in visual frequencies, such as a false-color image.

Inflow/Outflow

The cannula 130 can include the exuding ports 134 and the withdrawing ports 135, such as portions disposed to allow the passage of liquids or semi-liquids between an inside region and an outside region defined by the cannula 130. For example, those portions can include surfaces punctured by multiple small holes, surfaces defining strainers, or porous or semi-porous elements such as sponges.

The exuding ports 134 can also exude active or inactive reagents (such as florescent, radioactive, or other dyes; or such as medically effective biological, chemical, or chemotherapeutic substances; or such as micromechanical devices). For example, this can have the effect of allowing medical personnel 150 to locate the cannula 130 using noninvasive viewing (such as fluoroscopy or ultrasound). For another example, this can have the effect of allowing medical personnel 150 to affect bone, bony structure, or tissue in the intramedullary cavity 100.

In such cases, medical personnel 150 can use the emitters 132 to ablate or remove damaged or diseased tissue, or other untoward growths or substances. In alternative such cases, medical personnel 150 can use the exuding ports 134 to apply medication, pain-killers, anti-inflammatory agents, bone remodeling agents, or other useful substances, to tissue or other structures in the intramedullary cavity 100. In other alternative such cases, medical personnel 150 can use the exuding ports 134 to apply pharmaceuticals or other medication to particular locations selected by the medical personnel 150, e.g., disposing pharmaceuticals or other medication at strategic or optimum locations where they would be most effective (for treatment) or least risky (to the patient). When selecting medical personnel 150 in consideration of both relatively short-term and long-term release, uptake, metabolization, and elimination.

Guide Wire

The cannula 130 can include the guide wire 136, such as any device disposed to position and move the cannula 130 within the intramedullary cavity 100. For example, control and operation of the guide wire 136 can proceed by medical personnel 150. Medical personnel 150 can control or operate the guide wire 136 using the steering device 141, or using the computing devices 160 to control the steering device 141, as described herein.

FIG. 3

FIG. 3 shows a conceptual drawing of a method.

A method 300 includes flow points and method steps as described herein.

Although these flow points and method steps are (by the nature of the written word) described in a particular order, in the context of the invention there is no particular requirement for any particular order. This description does not limit the method to this particular order. They might be performed in a different order, or concurrently, or partially concurrently, or otherwise in a parallel, pipelined, quasi-parallel, or other manner. They might be performed in part, paused, and returned to for completion. They might be performed as co-routines or otherwise.

One or more portions of the method 300 are sometimes described as being performed by particular elements of the system described with respect to FIG. 1 and FIG. 2, or sometimes by "the method" itself. When a flow point or method step is described as being performed by "the method," it can be performed by one or more of those elements, by one or more portions of those elements, by an element not described with respect to the figure, by a combination or conjunction thereof, or otherwise.

A flow point 300A indicates a beginning of the method.

At a step 301, medical personnel 150 can initialize the computing devices 160. As part of this step, the computing devices 160 set/reset their state to an initial state consistent with the method 300 and this step.

At a step 302, medical personnel 150 can couple the cannula 130 to the guide wire 136, and couple the guide wire 136 to the computing devices 160.

At a step 303, medical personnel 150 can insert the cannula 130 (such as using the trocar tip 131) into extraosseous tissue, and guide the cannula 130 to an intramedullary cavity 100. As part of this step, medical personnel 150 use the computing devices 160 to visualize the position and movement of the cannula 130. Also as part of this step, medical personnel 150 use the guide wire 136 to control the position and movement of the cannula 130.

At a step 304, medical personnel 150 can dispose the cannula 130 in an intramedullary cavity 100.

At a step 305, medical personnel 150 can use the emitters 132 and the sensors 133 to gather information for the computing devices 160. For example, the sensors 133 can include one or more cameras, operating in visual or non-visual frequencies.

At a step 306, the computing devices 160 can perform instructions that convert the sensed information (gleaned from the emitters 132 and the sensors 133) into descriptive information. In one embodiment, the descriptive information includes a photograph or movie of an intramedullary cavity 100. In another embodiment, the descriptive information includes a detailed map of an intramedullary cavity 100.

At a step 307, the computing devices 160 can present, using the output elements 162, the photograph or movie or detailed map of the intramedullary cavity 100, or at least a portion thereof, to medical personnel 150. These medical personnel 150 can include first medical personnel 150 who were involved in the step 301, the step 302, and the step 303, or they can include second medical personnel 150. For example, the first medical personnel 150 can be involved in preparatory work for the patient, while the second medical personnel 150 can be involved in intramedullary surgery for the patient.

At a step 308, medical personnel 150 use the computing devices 160 with the input elements 163 thereof, and obtaining feedback with the output elements 162 thereof, can perform an operation on one of the intramedullary cavities 100.

For example, medical personnel 150 can, using the guide wire 136 or otherwise, insert one or more nails, rods, or other support structures, into one of the intramedullary cavities 100. This can have the effect of supporting the bone structure 110 against stress or damage (or further damage if already damaged).

For another example, medical personnel 150 can, using the exuding ports 134, or the withdrawing ports 135, medicate tissue in one of the intramedullary cavities 100. Alternatively, as part of this step, medical personnel 150 can, using the exuding ports 134, or the withdrawing ports 135, remove damaged or infected tissue, or lesions, from one of the intramedullary cavities 100. In alternative such cases, as part of this step, medical personnel 150 can, using the cannula 130, destroy infections or infected tissue.

For another example, medical personnel 150 can, using the emitters 132, perform one or more medical operations on tissue in one of the intramedullary cavities 100. In alternative such cases, as part of this step, medical personnel 150 can, using the cannula 130, place markers (such as biological, chemical, or radiological markers that show on fluoroscopy or other noninvasive measurement) that can be used to place bolts, pins, screws, or other set-points for use in attaching supports for bone structure 110. This can have the effect of allowing medical personnel 150 to support the bone structure 110 against stress or damage (or further damage if already damaged).

For another example, medical personnel 150 can, using the exuding ports 134 and the substance input conduits 144, infuse one or more specialized tissues within or near the intramedullary cavities 100 with one or more markers (such as dyes, florescent substances, or radiological substances). As part of this step, the specialized tissues can absorb or metabolize the marker substances. This can have the effect that medical personnel 150 can, using the computing device 160, identify one or more locations for the marker substances and the specialized tissues. As part of this step, medical personnel 150 can, using the withdrawing ports 135 and the substance output conduits 145, harvest the specialized tissues in relatively larger amounts or purer samples than could be achieved otherwise.

At a step 309, medical personnel 150 can remove the cannula 130 from the intramedullary cavity 100 and from the body. As part of this step, medical personnel 150 use the computing devices 160 to visualize the position and movement of the cannula 130. Also as part of this step, medical personnel 150 use the guide wire 136 to control the position and movement of the cannula 130.

At a flow point 300B, the method 300 is finished, and ready to be re-performed with respect to another medical procedure.

Alternative Embodiments

After reading this application, those skilled in the art would recognize that techniques shown in this application are applicable to more than just the specific embodiments shown herein. For example, the concept of intramedullary structure is intended to be broad, and can include any location in the body wholly or partially surrounded by, or near to, bone or bony structure; or in a body cavity wholly or partially enclosed by bone or bony structure. As used herein, bone or bony structure can include other substances or tissues closely related to bone and bony structures, such as cartilage, bone fragments, bone lesions, bone marrow or blood, cancellous bone, necrotic or osteoporotic bone structures, fats and other lipids, or otherwise.

While multiple embodiments are disclosed, including variations thereof, still other embodiments will become apparent to those skilled in the art from the enclosed detailed description, which shows and describes illustrative embodiments, which are capable of modifications in various aspects, all without departing from their scope or spirit. The drawings and detailed description are illustrative in nature and not restrictive. The claims are hereby incorporated by reference.

The invention claimed is:

1. A method for conducting an intramedullary procedure, the method including steps of inserting an assembly into a body, the assembly including a distal end coupled to a catheter and a guide wire, the guide wire coupled to a control element disposed outside the body, the distal end having a trocar tip having a shape disposed for penetration of bony tissue or structures, the shape being defined with a point and a set of surfaces, and insertion into a femur near a femoral neck, the set of surfaces being substantially transparent to electromagnetic radiation used for visualization;

steering the assembly using the guide wire from outside the body to dispose the assembly near to a bony structure inside the body;

using the distal end of the assembly to penetrate the bony structure to insert at least a portion of the assembly into an intramedullary cavity of the femur;

manipulating the distal end to the bony tissue in the femoral neck in the body, the bony tissue suffering from at least some findings of osteoporosis, the step of manipulating including emitting the electromagnetic radiation consisting of ultraviolet, infrared, or visible light from at least one emitter coupled to the distal end, and responsive to sensing effects of the electromagnetic radiation on the bony tissue with at least one sensor coupled to the distal end, providing signals describing three-dimensional imaging of the intramedullary cavity to a three-dimensional display outside the body, and moving the distal end in response to the guide wire to a position and orientation for treatment of the bony tissue;

using the catheter and a structure in the distal end to exude a marker substance in or near the femoral neck, the marker substance being disposed for florescent or radiological marking of the bony tissue, to receive cells or tissue samples from the bony tissue identified by the marker substance, and to exude a therapeutic substance to treat the at least some findings of osteoporosis in the bony tissue.

2. The method as in claim 1, including steps of using a steering device to move the position and the orientation of the distal end.

3. The method as in claim 1, including steps of sending instructions from medical personnel to the distal end; and using a robotic control to receive those instructions and to direct at least one action by the distal end.

4. The method as in claim 1, including steps of using information from the at least one sensor coupled to the distal end to determine the position and the orientation of the distal end within the bony tissue and structures.

5. The method as in claim 1, including steps of presenting to medical personnel a unified picture of the bony tissue and structures and the distal end, including the position and the orientation of the distal end within the bony tissue and structures.

6. A method for conducting an intramedullary procedure, the method including steps of inserting an assembly into a body, the assembly including a distal end coupled to a catheter and a guide wire, the guide wire coupled to a controller disposed outside the body, the distal end having a trocar tip having a shape disposed for penetration of bony tissue or structures, the shape being defined with a point and a set of surfaces, the surfaces being substantially transparent to electromagnetic radiation used for visualization;

steering the assembly using the guide wire from outside the body to dispose the assembly near to a bony structure inside the body;

using the distal end of the assembly to penetrate the bony structure to insert at least a portion of the assembly into an intramedullary cavity;

manipulating the distal end to near the bony tissue in a femoral neck in the body, the bony tissue suffering from at least some findings of osteoporosis, the steps of manipulating including the emitting electromagnetic radiation consisting of ultraviolet, infrared, or visible light emitted from at least one emitter coupled to the distal end, and responsive to sensing effects of the electromagnetic radiation on the bony tissue with at least one sensor coupled to the distal end, providing signals describing three-dimensional imaging of the intramedullary cavity to a three-dimensional display outside the body, and moving the distal end in response to the guide wire to a position and orientation for treatment of the bony tissue;

using the catheter and a structure in the distal end to exude a marker substance in or near the femoral neck, the marker substance being disposed for florescent or radiological marking of the bony tissue, to receive cells or tissue samples from the bony tissue identified by the marker substance.

7. The method as in claim 6, including steps of using the catheter and the structure in the distal end to exude a therapeutic substance to treat the at least some findings of osteoporosis in the bony tissue, wherein the therapeutic substance includes localized short- and long-acting agents.

8. The method as in claim 6, including steps of using the catheter and the structure in the distal end to exude a therapeutic substance to treat the at least some findings of osteoporosis in the bony tissue.

* * * * *